(12) United States Patent
Kunitsky et al.

(10) Patent No.: US 7,586,013 B2
(45) Date of Patent: Sep. 8, 2009

(54) METHOD FOR PREPARING HYDROXYSTYRENES AND ACETYLATED DERIVATIVES THEREOF

(75) Inventors: Keith Kunitsky, West Grove, PA (US); Mukesh C. Shah, Hockessin, DE (US); Steven W. Shuey, Landenberg, PA (US); Barry M. Trost, Los Altos Hills, CA (US); Mark Wagman, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 73 days.

(21) Appl. No.: 11/082,258

(22) Filed: Mar. 17, 2005

(65) Prior Publication Data

US 2005/0228191 A1 Oct. 13, 2005

Related U.S. Application Data

(60) Provisional application No. 60/556,861, filed on Mar. 26, 2004.

(51) Int. Cl.
*C07C 37/68* (2006.01)
(52) U.S. Cl. .................. 568/749; 568/579; 568/608; 568/654; 560/130
(58) Field of Classification Search .............. 568/130, 568/780, 579, 608, 654, 749; 560/130
See application file for complete search history.

(56) References Cited

U.S. PATENT DOCUMENTS

| 4,316,995 A | 2/1982 | Pittet et al. |
|---|---|---|
| 4,543,483 A | 9/1985 | Genrich |
| 5,041,614 A | 8/1991 | Aslam et al. |
| 5,084,533 A | 1/1992 | Shah et al. |
| 5,136,083 A | 8/1992 | Chosnek et al. |
| 5,151,546 A | 9/1992 | Shah et al. |
| 5,245,074 A | 9/1993 | Shah et al. |
| 5,274,060 A | 12/1993 | Schadeli |
| 5,324,804 A | 6/1994 | Steinmann |
| 5,453,481 A | 9/1995 | Sounik et al. |
| 5,563,289 A | 10/1996 | Sounik et al. |
| 5,578,687 A | 11/1996 | Sounik et al. |

FOREIGN PATENT DOCUMENTS

AU 7247129 10/1971

OTHER PUBLICATIONS

L.A.Cohen, and W.M.Jones☐☐A Study of pH Dependence in the Decarboxylation of p-Hydroxycinnamic Acid☐☐J.Am.Chem.Soc., 1907-1911, 82, 1960.*
Tapani Pyysalo et al., The Thermal Decarboxylation of some Substituted Cinnamic Acids, Lebensmittel-Wissenschraft u. Technol. 10(Food Science and Technology):145-147, 1977.
Louis A. Cohen et al., A Study of pH Dependence in the Decarboxylation of p-Hydroxycinnamic Acid, J. Amer. Chem. Soc., 82:1907-1911, 1960.
Richard C. Sovish, Preparation and Polymerization of p-Vinylphenol, J. Org. Chem., 24:1345-1347, 1959.
D. Munteanu et al., Synthesis of the Monomeric Antioxidant—3,5-di-tert-butyl-4-hydroxy-styrene by the thermal decomposition of trans-3,5-di-tert-butyl-4-hydroxycinnamic acid, Journal of Thermal Analysis, vol. 37:411-426, 1991.

* cited by examiner

*Primary Examiner*—Daniel M Sullivan
*Assistant Examiner*—Sudhakar Katakam

(57) ABSTRACT

A method is provided for the thermal decarboxylation of a phenolic substrate in the presence of a non-amine basic catalyst to produce a vinyl monomer. The product of the decarboxylation reaction may additionally be acetylated in the presence of an acetylating agent in the same reaction vessel.

20 Claims, No Drawings

METHOD FOR PREPARING HYDROXYSTYRENES AND ACETYLATED DERIVATIVES THEREOF

The invention relates to the field of organic synthesis. More specifically, the invention relates to a method for preparing hydroxystyrenes by thermal, base-catalyzed decarboxylation of phenolic substrates and the subsequent acetylation of the resulting product in a single reaction vessel, two-step process.

BACKGROUND OF THE INVENTION

Hydroxystyrenes, such as 4-hydroxystyrene (pHS) and acetylated derivatives thereof, such as 4-acetoxystyrene (pAS), are aromatic compounds that have potential utility in a wide variety of industrial applications. For example, these compounds have application in monomers for the production of resins, elastomers, adhesives, coatings, automotive finishes and inks, as well as in electronic materials. They may also be used as additives in elastomer and resin formulations.

A number of methods for the chemical synthesis of hydroxystyrenes and acetylated derivatives thereof are known. However, these methods require expensive reagents, harsh conditions, and give relatively low yields, typically between 30 to 63%. For example, Sovish (*J. Org. Chem.* 24:1345-1347 (1959)) describes a method for the preparation of 4-hydroxystyrene (also know as p-vinylphenol) from p-hydroxycinnamic acid (pHCA). The pHCA is decarboxylated in quinoline over copper powder at a temperature of about 225° C. The yield of 4-hydroxystyrene was about 41%.

Pittet et al. in U.S. Pat. No. 4,316,995 describe a method for preparing p-vinylphenol. In that method, p-hydroxybenzaldehyde is first reacted with malonic acid using ethylenediamine as catalyst to give pHCA, which is decarboxylated in situ at a temperature of 115 to 120° C. to form impure p-vinylphenol. The p-vinylphenol is isolated from the reaction mixture and reacted with acetic anhydride in the presence of a base, such as sodium hydroxide or potassium hydroxide, to form 4-acetoxystyrene, which is separated from the reaction mixture and hydrolyzed in the presence of a strong base to give purified p-vinylphenol. The yield of 4-vinylphenol was about 31%.

Schädeli in U.S. Pat. No. 5,274,060 describes a method for preparing 4-hydroxystyrene starting with pHCA. In that method, the pHCA is decarboxylated in dimethyl sulfoxide in the presence of an amine catalyst, i.e., 1,8-diazabicyclo[5,4-0]undec-7-ene, and hydroquinone at 135° C. to give 4-hydroxystyrene. The yield in that method was 63%.

Lala et al. in Australian Patent Application No. 7247129 describe a method for thermally decarboxylating ortho or para-hydroxyarylcarboxylic acids using an amine catalyst in an aprotic solvent to form the vinyl derivatives. Additionally, a method for preparing vinyl hydroxyaryl compounds by forming the hydroxyarylcarboxylic acid in situ, followed by thermal decarboxylation is described. The hydroxyarylcarboxylic acid is formed by reacting an aliphatic dicarboxylic acid or an aliphatic anhydride with a hydroxyarylaldehyde in a basic medium. The yields in those methods ranged from 15 to 60%.

Steinmann in U.S. Pat. No. 5,324,804 describes the synthesis of 3,4-dihydroxystyrene via the thermal decarboxylation of caffeic acid in dimethyl formamide at 150° C., in the absence of a catalyst. The yield obtained with that method was not given.

Munteanu et al. (*J. Thermal Anal.* 37:411-426 (1991)) describe the production of 3,5-di-tert-butyl-4-hydroxystyrene by the thermal decomposition of trans-3,5-di-tert-butyl-4-hydroxycinnamic acid with and without a non-amine basic catalyst in aprotic dipolar solvents. The reported yield was 95%. The thermal decarboxylation of other cinnamic acid derivatives is not described in the disclosure.

The thermal decarboxylation of substituted cinnamic acids has been studied in aqueous media. Pyysalo et al. (*Lebensmittel-Wissenschraft u. Technol.* 10 (Food Science and Technology):145-147 (1977)) describe the thermal decarboxylation of substituted cinnamic acid derivatives at pH 1 to 6 at 100° C. in aqueous buffer. Cohen et al. (*J. Amer. Chem. Soc.* 82:1907-1911 (1960)) describe the thermal decarboxylation of p-hydroxycinnamic acid in aqueous buffers at pH 1 to 12. The isolation of the decarboxylated product was not reported in those disclosures.

Therefore, the need exists for a method for preparing hydroxystyrenes and acetylated derivatives thereof that uses relatively inexpensive reagents, relatively mild conditions, and results in high yields.

Applicants have solved the stated problem by discovering a method for preparing hydroxystyrenes and acetylated derivatives thereof using relatively inexpensive reagents, under relatively mild conditions with yields up to 100%. The hydroxystyrenes are prepared by the thermal decarboxylation of a phenolic substrate in the presence of a non-amine basic catalyst. The acetylated derivatives are formed by reaction of the resulting hydroxystyrene with an acetylating agent in the same reaction vessel.

SUMMARY OF THE INVENTION

The invention relates to methods for the thermal decarboxylation of a phenolic substrate in the presence of a non-amine basic catalyst. The product of the decarboxylation reaction may additionally be acetylated in the presence of an acetylating agent in the same reaction vessel. Optionally, a polymerization inhibitor or retarder may be added to the reaction mixture. Yields of decarboxylated or acetylated product are typically in excess of 63%.

Accordingly it is within the scope of the invention to provide a method for the decarboxylation of a phenolic substrate to produce a vinyl monomer comprising the steps of:

a) providing a phenolic substrate having the general structure:

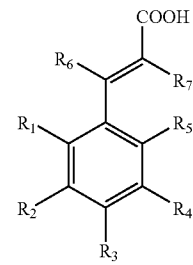

wherein $R_1$, $R_3$, and $R_5$ are H, OH, or $OCH_3$; $R_2$, and $R_4$ are H, OH, $OCH_3$ or linear or branched alkyl; $R_6$ and $R_7$ are H, halo, or cyano, provided that at least one of $R_1$, $R_3$, or $R_5$ is OH and that $R_2$, and $R_4$ are not both simultaneously t-butyl; and b) providing a reaction mixture comprising
   i) a non-amine basic catalyst; and
   ii) at least one polar organic solvent or polar organic solvent mixture; and c) contacting the phenolic substrate of (a) with the reaction mixture of (b) at a temperature of at least about 100° C. for a time sufficient for the decarboxylation of the phenolic substrate to a decarboxylated product. Optionally the decarboxylated product may be recovered by means well known in the art.

In an another embodiment the invention provides a method for the synthesis of an acetylated product from a phenolic substrate comprising the sequential steps of:

a) providing a phenolic substrate having the general structure:

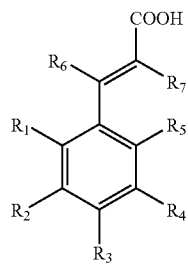

wherein $R_1$, $R_3$, and $R_5$ are H, OH, or $OCH_3$; $R_2$, and $R_4$ are H, OH, $OCH_3$ or linear or branched alkyl; $R_6$ and $R_7$ are H, halo, or cyano provided that at least one of $R_1$, $R_3$, or $R_5$ is OH, and;

b) providing a reaction mixture comprising:
  i) a non-amine basic catalyst; and
  ii) at least one polar, aprotic organic solvent or polar, aprotic organic solvent mixture; and c) contacting the phenolic substrate of (a) with the reaction mixture of (b) at a temperature of at least about 100° C. for a time sufficient for the decarboxylation of the phenolic substrate to form a decarboxylated product;

d) contacting the decarboxylated product of c) with an acetylating agent to produce an acetylated product having the general structure:

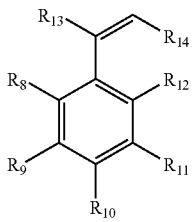

wherein $R_8$, $R_{10}$, and $R_{12}$ are H, $O(C=O)CH_3$, or $OCH_3$; $R_9$, and $R_{11}$ are H, OH, $OCH_3$ or linear or branched alkyl; $R_{13}$ and $R_{14}$ are H, halo, or cyano; provided that at least one of $R_8$, $R_{10}$, or $R_{12}$ is $O(C=O)CH_3$.

DETAILED DESCRIPTION OF THE INVENTION

The invention provides a method for preparing hydroxystyrenes via a thermal, non-amine base-catalyzed decarboxylation of phenolic substrates. The resulting hydroxystyrene may be acetylated in the same reaction vessel by addition of an acetylating agent. The method is useful because hydroxystyrenes and their acetylated derivatives have application as monomers for the production of resins, elastomers, adhesives, coatings, automotive finishes, inks and electronic materials, and additives in elastomer and resin formulations.

The following definitions are used herein and should be referred to for interpretation of the claims and the specification.

"p" means para.

"pAS" is the abbreviation used for para-acetoxystyrene which is also represented as p-acetoxystyrene or 4-acetoxystyrene.

"pHS" is the abbreviation used for para-hydroxystyrene which is also represented as p-hydroxystyrene or 4-hydroxystyrene.

"CA" means cinnamic acid.

The term "yield" as used herein refers to the amount of product produced in a chemical reaction. The yield is typically expressed as a percentage of the theoretical yield for the reaction. The term "theoretical yield" means the predicted amount of product to be expected based on the amount of substrate initially present and the stoichiometry of the reaction.

The term "polar" as applied to solvents of the invention refers to solvents characterized by molecules having sizable permanent dipole moments.

The term "aprotic" as applied to the solvents of the invention refers to a solvent that is incapable of acting as a labile proton donor or acceptor.

The term "protic" as applied to the solvents of the invention refers to a solvent that is capable of acting as a labile proton donor or acceptor.

The term "polar organic solvent mixture" refers to a mixture of organic solvents comprising at least one polar solvent.

The term "aprotic, polar organic solvent mixture" refers to a mixture of organic solvents comprising at least one aprotic, polar solvent.

"TAL" is the abbreviation used for tyrosine ammonia lyase.

"PAL" is the abbreviation used for phenylalanine ammonia lyase.

"PAH" is the abbreviation used for phenylalanine hydroxylase.

The term "TAL activity" refers to the ability of a protein to catalyze the direct conversion of tyrosine to pHCA.

The term "PAL activity" refers to the ability of a protein to catalyze the conversion of phenylalanine to cinnamic acid.

"pal" represents a gene that encodes an enzyme with PAL activity.

"tal" represents a gene that encodes an enzyme with TAL activity.

The term "PAL/TAL activity" or "PAL/TAL enzyme" refers to a protein, which contains both PAL and TAL activity. Such protein has at least some specificity for both tyrosine and phenylalanine as an enzymatic substrate.

The term "P-450/P-450 reductase system" refers to a protein system responsible for the catalytic conversion of cinnamic acid to pHCA. The P-450/P-450 reductase system is one of several enzymes or enzyme systems known in the art that performs a cinnamate 4-hydroxylase function. As used herein the term "cinnamate 4-hydroxylase" will refer to the general enzymatic activity that results in the conversion of cinnamic acid to pHCA, whereas the term "P-450/P-450 reductase system" will refer to a specific binary protein system that has cinnamate 4-hydroxylase activity.

All ranges given herein include the end of the ranges and also all the intermediate range points.

The instant invention comprises a method for producing vinyl monomers, specifically, hydroxystyrenes, having the general formula:

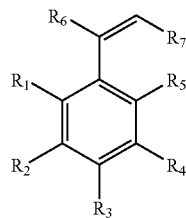

wherein $R_1$, $R_3$, and $R_5$ are H, OH, or $OCH_3$; $R_2$, and $R_4$ are H, OH, $OCH_3$ or linear or branched alkyl; $R_6$ and $R_7$ are H, halo, or cyano provided that at least one of $R_1$, $R_3$, or $R_5$ is OH, where it is preferred if that $R_2$, and $R_4$ are not both simultaneously t-butyl. Examples of hydroxystyrenes that may be produced by the method of the instant invention include, but are not limited to 4-hydroxystyrene, 3-methoxy-4-hydroxystyrene, 3,5-dimethoxy-4-hydroxystyrene, 3,4-dihydroxystyrene, 2-hydroxystyrene and α-cyano-4-hydroxystyrene.

Additionally, the resulting hydroxystyrenes may be acetylated by addition of an acetylating agent to the reaction vessel to give acetylated products having the general structure:

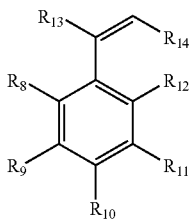

wherein $R_8$, $R_{10}$, and $R_{12}$ are H, $O(C=O)CH_3$, or $OCH_3$; $R_9$, and $R_{11}$ are H, OH, $OCH_3$ or linear or branched alkyl; $R_{13}$ and $R_{14}$ are H, halo, or cyano, provided that at least one of $R_8$, $R_{10}$, or $R_{12}$ is $O(C=O)CH_3$. Examples of acetylated products include, but are not limited to 4-acetoxystyrene, 3-methoxy-4-acetoxystyrene, 3,5-dimethoxy-4-acetoxystyrene, 3,4-diacetoxystyrene, 2-acetoxystyrene, and α-cyano-4-acetoxystyrene.

Phenolic Substrates

The phenolic substrates for use in the invention have the general structure:

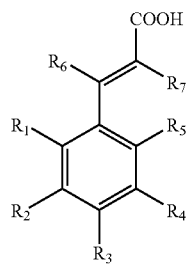

wherein $R_1$, $R_3$, and $R_5$ are H, OH, or $OCH_3$; $R_2$, and $R_4$ are H, OH, $OCH_3$ or linear or branched alkyl; $R_6$ and $R_7$ are H, halo, or cyano provided that at least one of $R_1$, $R_3$, or $R_5$ is OH. Examples of suitable phenolic substrates include, but are not limited to 4-hydroxycinnamic acid, ferulic acid, sinapinic acid, caffeic acid, 2-hydroxycinnamic acid, and α-cyano-4-hydroxycinnamic acid. It was discovered that high yields of the decarboxylated product were obtained even with non-sterically hindered phenol substrates, which are more prone to product decomposition than sterically hindered phenols. Sterically hindered phenols are herein defined as phenols having large, bulky groups, such as t-butyl, at both $R_2$ and $R_4$ positions. Non-sterically hindered phenols are phenols that do not have large, bulky groups at both $R_2$, and $R_4$ positions. Non-sterically hindered phenol substrates include, but are not limited to, phenols wherein at least one of $R_2$ or $R_4$ is H, OH, $OCH_3$, methyl, ethyl, or propyl. Moreover, it was discovered that high yields of decarboxylated product were obtained even with ortho unsubstituted phenol substrates, which are also prone to product decomposition. Ortho unsubstituted phenols are herein defined as phenols wherein at least one of $R_2$ or $R_4$ is H.

These phenolic substrates may be obtained in a number of ways. For example, 4-hydroxycinnamic acid (pHCA), predominantly in the trans form, is available commercially from companies such as Aldrich (Milwaukee, Wis.) and TCI America (Portland, Oreg.). Additionally, pHCA may be prepared by chemical synthesis using any method known in the art. For example, pHCA may be obtained by reacting malonic acid with para-hydroxybenzaldehyde as described by Pittet et al. in U.S. Pat. No. 4,316,995, or by Alexandratos in U.S. Pat. No. 5,990,336. Alternatively, pHCA may also be isolated from plants (R. Benrief et al. *Phytochemistry* 47:825-832 (1998) and U.S. patent application Publication No. 20020187207). In one embodiment, the source of pHCA is from bioproduction using a production host. In another embodiment, the production host is a recombinant host cell, which may be prepared using standard DNA techniques. These recombinant DNA techniques are described by Sambrook, J., Fritsch, E. F. and Maniatis, T. *Molecular Cloning: A Laboratory Manual*, Second Edition, Cold Spring Harbor Laboratory Press, Cold Spring Harbor, N.Y. (1989), incorporated herein by reference.

In one embodiment, pHCA is produced as described by Qi et al. in U.S. patent application Publication No. 20030079255, incorporated herein by reference. According to that disclosure, pHCA may be produced using a recombinant microorganism engineered to express at least one gene encoding a phenylalanine hydroxylase (PAH) activity and at least one gene encoding a tyrosine ammonia lyase (TAL) activity. This transformed microorganism metabolizes a fermentable carbon source, such as glucose, to phenylalanine, which is converted to tyrosine by PAH. The tyrosine produced is converted to pHCA by the TAL enzyme. Any suitable enzyme possessing a TAL activity may be used. For example, an enzyme having both PAL and TAL (PAL/TAL) activity may be used. TAL enzymes, produced through mutagenesis of wild-type yeast PAL enzymes to have enhanced TAL activity, may also be used, as described by Gatenby et al. in U.S. Pat. No. 6,368,837. Alternatively, an inducible TAL enzyme from the yeast *Trichosporon cutaneum*, as described by Breinig et al. in U.S. patent application Publication No. 20040023357 or a bacterial TAL enzyme such as that described by Kyndt et al. (*FEBS Lett.* 512:240-244 (2002)) or by Huang et al. in U.S. patent application Publication No. 20040059103) may be used.

In an another embodiment, pHCA is produced by any one of the methods disclosed by Gatenby et al. supra, incorporated herein by reference. For example, pHCA may be produced using a recombinant microorganism engineered to express a gene encoding a yeast PAL activity and genes encoding a plant P-450/P-450 reductase system. This transformed microorganism metabolizes a fermentable carbon source, such as glucose, to phenylalanine, which is converted to cinnamic acid (CA) by the PAL enzyme. CA is subsequently converted to pHCA by the action of the P-450/P-450 reductase system. Alternatively, pHCA may be produced using a recombinant microorganism expressing a gene encoding a TAL activity. The TAL enzyme converts tyrosine directly to pHCA. Any suitable TAL enzyme may be used, as described supra.

In another embodiment, pHCA is produced using a two-stage fermentation as described by Ben-Bassat in copending and commonly owned U.S. Patent Application No. 60/563,633, incorporated herein by reference. The first stage comprises providing a microbial production host having an enhanced ability to produce the aromatic amino acid tyrosine (an over-producer). These cells are grown at physiological pH to a point where tyrosine is accumulated in the growth medium. During the second stage of the fermentation the cells are contacted with a source of TAL at a pH of about 8.0 to about 11.0. During this stage tyrosine is converted to pHCA at relatively high rates and yields. Alternatively, the two stages may be done as two separate steps, wherein the tyrosine is isolated from the fermentation medium of the first step and then is contacted with the source of TAL.

For the bioproduction of pHCA, the microorganism to be used is cultured in a fermentor in a suitable growth medium. Any suitable fermentor may be used including a stirred tank fermentor, an airlift fermentor, a bubble fermentor, or any combination thereof. Materials and methods for the maintenance and growth of microbial cultures are well known to those in the art of microbiology or fermentation science (See for example, Bailey et al., *Biochemical Engineering Fundamentals*, second edition, McGraw Hill, New York, 1986). The bioproduced pHCA may be isolated from the fermentation medium for use in the invention using methods known in the art. For example, solids may be removed from the fermentation medium by centrifugation. Then, the pHCA may be precipitated by acidification of the medium and recovered by centrifugation. If desired, the pHCA may be further purified, for example, using organic solvent extraction.

Similarly, ferulic acid, sinapinic acid, and caffeic acid are available commercially from companies such as Aldrich (Milwaukee, Wis.) and TCI America (Portland, Oreg.). Alternatively as these substrates are all natural plant products, comprising elements of the lignin biosynthetic pathway, they may be readily isolated from plant tissue (see for example Jang et al., *Archives of Pharmacal Research* (2003), 26(8), 585-590; Matsufuji et al., *Journal of Agricultural and Food Chemistry* (2003), 51(10), 3157-3161; WO 2003046163; Couteau et al, *Bioresource Technology* (1998), 64(1), 17-25; and Bartolome et al., *Journal of the Science of Food and Agriculture* (1999), 79(3), 435-439). Additionally, methods of chemical synthesis are known for a number of the more common phenolic substrates (see for example WO 2002083625 ("Preparation of ferulic acid dimers and their pharmaceutically acceptable salts, and use thereof for treating dementia") JP 2002155017 ("Preparation of caffeic acid from ferulic acids"); and Taniguchi et al., *Anticancer Research* (1999), 19(5A), 3757-3761). The preparation of alkylated pHCA derivatives is described by Lala et al. in Australian Patent Application No. 7247129.

Non-Amine Basic Catalysts

The method of the invention makes use of a non-amine basic catalyst. A non-amine basic catalyst is any basic compound capable of facilitating the present reactions that does not contain amines. By way of comparison examples of amine containing catalysts are pyridine and ethylenediamine. Virtually any non-amine basic catalyst may be used that is compatible with the reaction conditions of the invention, where metallic salts and particularly potassium salts or acetate salts are preferred. Catalysts particularly suitable in the present invention include, but are not limited to, potassium acetate, potassium carbonate, potassium hydroxide, sodium acetate, sodium carbonate, sodium hydroxide and magnesium oxide.

All of the non-amine catalysts of the invention are available commercially from, for example, EM Science (Gibbstown, N.J.) or Aldrich (Milwaukee, Wis.).

The optimum concentration of non-amine basic catalyst will vary depending on the concentration of substrate, nature of the solvent used and reaction conditions. Typically concentrations of about 1 mol % to about 30 mol %, relative to the substrate, in the reaction mixture are preferred.

Organic Solvents

For the decarboxylation reaction alone, a wide variety of organic solvents may be used, including both aprotic, polar organic solvents and protic, polar organic solvents. A single protic, polar solvent or a single aprotic, polar solvent may be used. Additionally, mixtures of aprotic, polar solvents, mixtures of protic, polar solvents, mixtures of aprotic and protic, polar solvents, and mixtures of aprotic or protic solvents with nonpolar solvents may be used, wherein aprotic, polar solvents or mixtures thereof are preferred. Suitable aprotic, polar solvents include, but are not limited to, N,N-dimethylformamide, 1-methyl-2-pyrrolidinone, N,N-dimethylacetamide, dimethylsulfoxide, hexamethylphosphoramide, and hexamethylphosphorous triamide. Suitable protic, polar solvents include, but are not limited to, di(propylene glycol)methyl ether (Dowanol™ DPM), di(ethylene glycol)methyl ether, 2-butoxyethanol, ethylene glycol, 2-methoxyethanol, propylene glycol methyl ether, n-hexanol, and n-butanol.

For the two-step decarboxylation-acetylation process, organic solvents should have the net characteristics of being both aprotic and polar. A single aprotic, polar solvent may be used, or a mixture of aprotic, polar solvents may be used. Alternatively, an aprotic, polar solvent may be used in combination with a non-polar solvent; however, protic solvents are undesirable because they tend to consume acetylating agent due to their reactivity. Solvents particularly suitable in the two step process of the invention include, but are not limited to, N,N-dimethylformamide, 1-methyl-2-pyrrolidinone, N,N-dimethylacetamide, dimethylsulfoxide, hexamethylphosphoramide, and hexamethylphosphorous triamide.

Polymerization Inhibitors

Polymerization inhibitors are useful but not required in the methods of the invention. Any suitable polymerization inhibitor that is tolerant of the temperatures required for the decarboxylation reaction as described in the invention may be used. Examples of suitable polymerization inhibitors include, but are not limited to, hydroquinone, hydroquinone monomethylether, 4-tert-butyl catechol, phenothiazine, N-oxyl(nitroxide) inhibitors, including Prostab® 5415 (bis(1-oxyl-2,2,6,6-tetramethylpiperidine-4-yl)sebacate, CAS#2516-92-9, available from Ciba Specialty Chemicals, Tarrytown, N.Y.), 4-hydroxy-TEMPO (4-hydroxy-2,2,6,6-tetramethylpiperidin-1-yloxy, CAS#2226-96-2, available from TCI America) and Uvinul® 4040 P (1,6-hexamethylene-bis(N-formyl-N-

(1-oxyl-2,2,6,6-tetramethylpiperidine-4-yl)amine, available from BASF Corp., Worcester, Mass.).

Polymerization Retarders

In some instances it may be advantageous to use a polymerization retarder in the present reaction in combination with the polymerization inhibitor. Polymerization retarders are well known in the art and are compounds that slow down the polymerization reaction but cannot prevent it altogether. Common retarders are aromatic nitro compounds such as dinitro-ortho-cresol (DNOC) and dinitrobutylphenol (DNBP). Methods for the preparation of polymerization retarders are common and well known in the art (see for example U.S. Pat. No. 6,339,177; Park et al., *Polymer* (Korea) (1988), 12(8), 710-19) and their use in the control of styrene polymerization is well documented (see for example Bushby et al., *Polymer*(1998), 39(22), 5567-5571).

Reaction Conditions

The phenolic substrate, the non-amine basic catalyst, and the organic solvent are added to a reaction vessel to form a reaction mixture. Any suitable reaction vessel may be used.

Reaction temperatures may vary depending on the concentration of substrate, the stability of the product formed, choice of catalyst and yield desired. Typically, temperatures of at least about 100° C. are suitable where temperatures in the range of at least about 100° C. to about 200° C. are consistent with effective production of product. For the reaction using 4-hydroxycinnamic acid as substrate, the preferred temperature range is from about 120° C. to about 150° C. For substrates that give a less stable product, e.g., caffeic acid, lower temperatures in the range of about 100° C. to about 120° C. are used. Higher temperatures in the range of about 150° C. to about 200° C. may be used with substrates that give a more stable product, e.g., 3,5-dimethyl-4-hydroxycinnamic acid.

The reaction may be carried out at a pressure ranging from atmospheric pressure to about 1000 psig (6895 kPa) in addition a pressure of about 500 psig (3447 kPa) may be used. The pressure may be adjusted using an inert gas such as nitrogen. For reactions at elevated pressures, any conventional pressure reaction vessel may be used including, but not limited to shaker vessels, rocker vessels, and stirred autoclaves.

There is no limit on the time for the reaction; however, most reactions will run in less than four hours and reaction times of about 45 minutes to about 180 minutes are typical.

Acetylation of Hydroxystyrenes

In one embodiment, the decarboxylated phenolic product is converted to an acetylated derivative by adding an acetylating agent directly to the reaction mixture after completion of the decarboxylation reaction. Typically the acetylating agent is added in excess where a concentration of at least 1 mole equivalent as compared to the substrate is preferred. Suitable acetylating agents include, but are not limited to acetic anhydride, acetyl chloride, and acetic acid. In one embodiment, the acetylating agent is acetic anhydride.

The acetylation reaction may be carried out with high yield at temperatures ranging from about 25° C. to about 150° C., in addition ranging from about 100° C. to about 140° C., at a pressure ranging from atmospheric pressure to about 1000 psig (6895 kPa). One skilled in the art will recognize that a temperature at which both the substrate and the catalyst are soluble should be used. The simplest approach is to add the acetylating agent just after completion of the decarboxylation reaction step and to perform the acetylation at the same temperature as the decarboxylation reaction.

Isolation and Purification of Decarboxylated and Acetylated Product

After completion of the reaction, the decarboxylated product or the acetylated product may be isolated using any suitable method known in the art. For example, the reaction mixture may be poured onto ice water and extracted into an organic solvent, such as ethyl acetate or diethylether. Then, the product may be recovered by removing the solvent using evaporation at reduced pressure. In one embodiment, the product yield of the hydroxystyrene product is at least 63% of the theoretical yield. In another embodiment, the yield of the acetylated product is at least 63% of the theoretical yield.

The decarboxylated product or the acetylated derivative thereof may be further purified using recrystallization, vacuum distillation, flash distillation, or chromatographic techniques that are well known in the art.

The resultant hydroxystyrene or acetylated derivative thereof may then be used as monomers for the production of resins, elastomers, adhesives, coatings, automotive finishes, inks, and as additives in elastomer and resin formulations.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "sec" means second(s), "mL" means milliliter(s), "L" means liter(s), "µL" means microliter(s), "µm" means micrometer(s), "mol" means mole(s), "mmol" means millimole(s), "g" means gram(s), "mg" means milligram(s), "ppm" means parts per million, "M" means molar concentration, "m" means molar concentration, "eq" means equivalents, "v/v" means volume to volume ratio, "Pa" means pascal, "mPa" means millipascal, "psig" means pounds per square inch gauge, "MHz" means megahertz, "TLC" means thin layer chromatography, "HPLC" means high performance liquid chromatography, "LC-MS" means liquid chromatography-mass spectrometry, "NMR" means nuclear magnetic resonance spectrometry, "DMF" means N,N-dimethylformamide, "DMAc" means N,N-dimethylacetamide, "NMP" means 1-methyl-2-pyrrolidinone, "nd" means not determined, "kPa" means kilopascal(s), "rpm" means revolutions per minute, and "UV" means ultraviolet.

General Methods:

Reagents:

Para-hydroxycinnamic acid was obtained from Aldrich (Milwaukee, Wis.) or TCI America (Portland, Oreg.), unless otherwise noted; 3,4 dihydroxycinnamic acid was obtained from Aldrich. All solvents were reagent grade and were obtained from Aldrich. The basic catalysts used were obtained from Aldrich or EM Science (Gibbstown, N.J.). The polymerization inhibitor Prostab® 5415 was obtained from Ciba Specialty Chemicals, Tarrytown, N.Y.

Analytical Methods:

TLC Method:

TLC was done using Silica gel 60F$_{254}$ (EM Science) as the solid support. A 1:1 mixture of ethylacetate and hexanes was used as the mobile phase for the analysis of pHCA, and a 1:4 mixture of ethylacetate and hexanes was used for pHS. The samples were compared to authentic samples of pHCA and pHS. The TLC plates were observed using an ultra-violet lamp at 254 nm.

HPLC Methods:

Method 1: An Agilent 1100 HPLC system (Agilent Technologies, Wilmington, Del.) was used with a reverse-phase Zorbax SB-C8 column (4.6 mm×150 mm, 3.5 μm, supplied by MAC-MOD Analytical Inc., Chadds Ford, Pa.). The HPLC separation was achieved using a gradient combining two solvents: Solvent A, 0.1% trifluoroacetic acid in HPLC grade water and Solvent B, 0.1% trifluoroacetic acid in acetonitrile. The mobile phase flow rate was 1.0 mL/min. The solvent gradient used is given in Table 1. A temperature of 45° C. and a sample injection of 5 μL were used.

TABLE 1

Solvent Gradient Used for HPLC Method 1

| Time (min) | Solvent A | Solvent B |
|---|---|---|
| 0 | 95% | 5% |
| 8 | 20% | 80% |
| 10 | 20% | 80% |
| 11 | 95% | 5% |

After each run, the column was re-equilibrated for 5 min with a solvent mixture of 95% A and 5% B.

Suitable calibration curves were generated using standard pHS solutions. The pHS for the standards was prepared from acetoxystyrene using a method similar to that described by Leuteritz et al. (*Polymer Preprints* 43(2):283-284 (2002)). The calibration curves were used to determine wt % of pHCA and pHS in each sample from HPLC peak areas. With this information and the total weight of the reaction mixture at the time of sampling, the % conversion of pHCA and the % yield of pHS were calculated.

Method 2: The Agilent 1100 HPLC system was used with a reverse-phase Zorbax SB-C18 column (4.6 mm×150 mm, 3.5 μm, supplied by Agilent Technologies). The HPLC separation was achieved using a gradient combining two solvents: Solvent A, 0.1% trifluoroacetic acid in HPLC grade water and Solvent B, 0.1% trifluoroacetic acid in acetonitrile. The mobile phase flow rate was 1.25 mL/min. The solvent gradient used is given in Table 2. A temperature of 40° C. and a sample injection of 1 μL were used.

TABLE 2

Solvent Gradient Used for HPLC Method 2

| Time (min) | Solvent A | Solvent B |
|---|---|---|
| 0 | 90% | 10% |
| 35 | 35% | 65% |
| 35.1 | 90% | 10% |
| 45 | 90% | 10% |

Suitable calibration curves were generated and used to determine wt % of pHCA and pHS in each sample from HPLC peak areas, as described above. With this information and the total weight of the reaction mixture at each time (including a correction for the loss of $CO_2$ upon decarboxylation), the weight and moles of pHCA and pHS versus time were calculated.

Method 3: The Agilent 1100 HPLC system was used with a reverse-phase Zorbax XDB-C18 column, 2.1×50 mm (supplied by Agilent Technologies). The HPLC separation was achieved using a gradient combining two solvents: Solvent A, HPLC grade water+0.05% trifluoroacetic acid, and Solvent B, HPLC grade acetonitrile+0.05% trifluoroacetic acid. The gradient was 95% A to 0% A over 4.5 minutes, hold 0.5 minutes, then return to initial conditions. The mobile phase flow rate was 0.8 mL/min. A temperature of 60° C. and a sample injection of 1 μL were used.

Method 4: The Agilent 1100 HPLC system was used with a reverse-phase Zorbax SB-C18 column (4.6 mm×150 mm, 3.5 μm, supplied by Agilent Technologies). The HPLC separation was achieved using a gradient combining two solvents: Solvent A, 0.1% trifluoroacetic acid in HPLC grade water and Solvent B, 0.1% trifluoroacetic acid in acetonitrile. The mobile phase flow rate was 1.0 mL/min. The solvent gradient used is given in Table 3. A temperature of 40° C. and a sample injection of 1 μL were used.

TABLE 3

Solvent Gradient Used for HPLC Method 4

| Time (min) | Solvent A | Solvent B |
|---|---|---|
| 0 | 95% | 5% |
| 10 | 100% | 0% |
| 12 | 100% | 0% |
| 12.5 | 95% | 5% |

Suitable calibration curves were generated as described above and used to determine wt % of pHCA and pHS in each sample from HPLC peak areas. With this information and the total weight of the reaction mixture at each time (including a correction for the loss of $CO_2$ upon decarboxylation), the weight and moles of pHCA and pHS versus time were calculated.

$^1$H NMR:

The proton NMR data was obtained using a Bruker DRX (Bruker NMR, Billerica, Mass.) at 500 MHz.

LC-MS Method:

A Hewlett Packard LC/MSD Series 1100 instrument (Agilent Technologies, Wilmington, Del.) was used for the LC-MS analysis. A Zorbax Eclipse XDB-C18 column (2.1 mm×50 mm, MAC-MOD Analytical Inc.) was used in the LC separation with a solvent gradient consisting of two solvents, solvent A, 0.05% trifluoroacetic in water and solvent B, 0.05% trifluoroacetic acid in acetonitrile. The gradient was from 95% solvent A to 0% solvent A over 4.5 min, followed by 2.5 min with 0% solvent A and then returned to 95% solvent A, with a flow rate of 0.8 mL/min. The LC separation was done at a temperature of 60° C. with detection at 220 nm.

Examples 1-13

Preparation of 4-Hydroxystyrene by Decarboxylation of Para-hydroxycinnamic Acid

The purpose of these Examples was to prepare 4-hydroxystyrene by the thermal, base-catalyzed decarboxylation of para-hydroxycinnamic acid using various combinations of a basic catalyst and solvent in the presence of a polymerization inhibitor.

In these Examples, para-hydroxycinnamic acid was used as the phenolic substrate at a concentration of 1 M in 1 mL of the solvent. The basic catalyst and the solvent used in these Examples are given in Table 4. The basic catalyst was used at a concentration of 3 mol % relative to the phenolic substrate.

The polymerization inhibitor Prostab® 5415 was used in all reactions at a concentration of 1000 ppm. The reactions were carried out in a custom-built, mini-block pressure reactor at a temperature of 150° C. under 500 psig nitrogen. The mini-block pressure reactor is a stainless steel reactor designed to hold eight 1-2 mL glass vials, each containing a separate reaction mixture. The reactor has a maximum rating of 260° C. at 1250 psig. After the reactor was loaded with the glass vials containing the reaction mixtures, it was sealed, pressurized with nitrogen and heated in a block heater.

After a reaction time of 1 h, the reactor was depressurized and a sample of the reaction mixture was analyzed by HPLC using Method 1, as described above. The amount of phenolic substrate consumed in the reaction (pHCA conversion) and the yield of 4-hydroxystyrene for each Example are summarized in Table 4.

TABLE 4

Basic Catalyst and Solvent Combinations Used in Examples 1-13

| Example | Solvent | Basic Catalyst | pHCA Conversion % | Product Yield % |
|---|---|---|---|---|
| 1 | DMF | potassium acetate | 99.8 | 88.8 |
| 2 | DMAc | sodium methoxide | 90.7 | 81.5 |
| 3 | 2-heptanone | potassium carbonate | 64.2 | 68.2 |
| 4 | Toluene/DMF (80/20 v/v) | magnesium oxide | 98.9 | 55.0 |
| 5 | γ-Butyrolactone | potassium hydroxide | 99.9 | 78.7 |
| 6 | DMF | potassium hydroxide | 99.7 | 95.2 |
| 7 | Diglyme | potassium acetate | 7.2 | 30.8 |
| 8 | 2-heptanone | sodium methoxide | −7.7 | 9.6 |
| 9 | Toluene/DMF | potassium carbonate | 67.1 | 49.0 |
| 10 | γ-Butyrolactone | magnesium oxide | 3.7 | 20.4 |
| 11 | DMF | potassium carbonate | 99.8 | 84.9 |
| 12 | DMF | potassium acetate | 99.0 | 106.9 |
| 13 | NMP | potassium acetate | 99.7 | 107.2 |

As can be seen from the results in Table 4, the highest product yields were obtained in DMF, DMAc, and NMP using potassium acetate, sodium methoxide, potassium hydroxide, and potassium carbonate as the basic catalyst.

Example 14

Preparation of 4-Hydroxystyrene by Decarboxylation of Para-hydroxycinnamic Acid Using Potassium Acetate as Basic Catalyst in DMF The purpose of this Example was to prepare 4-hydroxystyrene by the thermal, base-catalyzed decarboxylation of para-hydroxycinnamic acid using potassium acetate (10 mol %) as the basic catalyst in DMF in the presence of a polymerization inhibitor (1000 ppm Prostab® 5415). To a 3-neck, round-bottom flask was added pHCA (5 g, 30.458 mmol, 1 eq), 30 mL of DMF (to make a 1 M solution of pHCA), 1000 ppm Prostab® 5415 (5 mg), and potassium acetate (0.3 g, 10 mol %). The reaction was performed under nitrogen with stirring and with a reflux condenser. The reaction was heated to 150° C. using an oil bath and temperature controller (with overtemp protection). The potassium acetate was not soluble at room temperature, but dissolved as heat was applied, giving a pale yellow solution. The reaction was monitored by TLC, as described supra. After 1.5 h at 150° C., the reaction was complete, as determined by TLC. The heat was discontinued and the reaction mixture was allowed to cool to room temperature. The reaction mixture was then poured onto 100 mL of ice water, which was saturated with sodium chloride, and extracted twice with ethyl acetate (75 mL portions). The organic layers from the two extractions were combined and washed with 100 mL of 2% NaHCO$_3$ solution, and then washed with 100 mL of water. The organic layer was dried over Na$_2$SO$_4$, filtered and concentrated by evaporation on a rotary evaporator. The residue was stored at −20° C. overnight. Then, the residue was dried further under reduced pressure (10 Pa) to give 3.44 g of a light yellow/tan solid (94% of the theoretical yield). The product was analyzed using $^1$H NMR.

$^1$H NMR (500 MHz, MeOD): δ (ppm) 7.998 (0.04H, s), 7.275 (2H, ABq, J=9.0 Hz), 6.758 (2H, ABq, J=9.1 Hz), 6.65 (1H, dd, J=17.6 and 11.0 Hz), 5.575 (1H, dd, J=17.6 and 1.1 Hz), 5.048 (1H, dd, J=11.0 and 1.4 Hz).

Example 15

Preparation of 4-Hydroxystyrene by Decarboxylation of Para-hydroxycinnamic Acid Using Potassium Acetate as Basic Catalyst in DMF The purpose of this Example was to prepare 4-hydroxystyrene by the thermal, base-catalyzed decarboxylation of para-hydroxycinnamic acid using potassium acetate (3 mol %) as the basic catalyst in DMF in the presence of a polymerization inhibitor (100 ppm Prostab® 5415).

The reaction was carried out as described in Example 14, except that 100 ppm Prostab® 5415 (0.5 mg, added as 250 μL of a 2 mg/mL solution in DMF) and 3 mol % potassium acetate (90 mg) were used. The product was isolated as described in Example 14, resulting in 3.82 g of a golden-yellow semi-solid (104.6% of the theoretical yield). The product was analyzed using $^1$H NMR.

$^1$H NMR (500 MHz, MeOD): δ (ppm) 7.993 (0.22H, s), 7.275 (2H, ABq, J=8.6 Hz), 6.76 (2H, ABq, J=8.6 Hz), 6.65 (1H, dd, J=17.6 and 10.9 Hz), 5.577 (1H, dd, J=17.6 and 1.4 Hz), 5.048 (1H, dd, J=11.0 and 0.7 Hz).

Example 16

Preparation of 4-Acetoxystyrene by Decarboxylation of Para-hydroxycinnamic Acid Followed by Acetylation in a Single Vessel Reaction The purpose of this Example was to prepare 4-acetoxystyrene using the thermal, base-catalyzed decarboxylation of para-hydroxycinnamic acid, followed by acetylation of the resulting 4-hydroxystyrene with acetic anhydride in a two-step, single vessel reaction. Prostab® 5415 at a concentration of 100 ppm was used as the polymerization inhibitor.

To a 3-neck round-bottom flask was added pHCA (5 g, 30.458 mmol, 1 eq), 30 mL of DMF (to make a 1 M solution in pHCA), 100 ppm Prostab® 5415 (0.5 mg, added as 250 μL of a 2 mg/mL solution in DMF) and potassium acetate (30 mg, 1 mol %). The reaction was performed under nitrogen with stirring and with a reflux condenser. The reaction was heated to 150° C. with an oil bath and temperature controller (with overtemp protection). The potassium acetate was not soluble at room temperature, but dissolved as heat was applied, giving a pale yellow solution. The reaction was monitored by TLC, as described supra. After 2 h at 150° C., the reaction appeared to be complete, as determined by TLC. Then, the reaction temperature was reduced to 140° C. and acetic anhydride (4.32 mL, 45.687 mmol, 1.5 eq) was added dropwise to the reaction mixture, which was maintained at 140° C. The color of the reaction mixture became lighter. The reaction was complete after 0.75 h, as determined using TLC. Heating was discontinued and the reaction mixture was allowed to cool to room temperature. The reaction mixture was stored at −20° C. overnight.

The 4-acetoxystyrene was isolated using the procedure described in Example 14 for the isolation of 4-hydroxystyrene, resulting in 5.39 g of a pale yellow, semi-solid (109% of the theoretical yield). The product was analyzed using $^1$H NMR. The greater than theoretical yield obtained and the nature of the product (i.e., pale yellow semi-solid) suggest that the product contained some impurities.

$^1$H NMR (500 MHz, CDCl$_3$): δ (ppm) 7.40 (2H, ABq, J=8.6 Hz), 7.045 (2H, ABq, J=8.5 Hz), 6.693 (1H, dd, J=17.5 and 11.0 Hz), 5.693 (1H, dd, J=17.6 and 0.7 Hz), 5.234 (1H, dd, J=10.9 and 0.8 Hz), 2.29 (2.64H, s)

Example 17

Preparation of 4-Acetoxystyrene by Decarboxylation of Para-hydroxycinnamic Acid Followed by Acetylation in a Single Vessel Reaction The purpose of this Example was to prepare 4-acetoxystyrene using the thermal, base-catalyzed decarboxylation of para-hydroxycinnamic acid, followed by acetylation of the resulting 4-hydroxystyrene with acetic anhydride in a two-step, single vessel reaction. Prostab® 5415 at a concentration of 1000 ppm was used as the polymerization inhibitor.

The decarboxylation and acetylation reactions were carried out as described in Example 16, except that 1000 ppm Prostab® 5415 (5 mg) was used as the polymerization inhibitor. The 4-acetoxystyrene product was isolated as described in Example 16, resulting in 4.82 g of a yellow oil (97.5% of the theoretical yield). The product was analyzed using $^1$H NMR. $^1$H NMR (500 MHz, CDCl$_3$): δ (ppm) 7.40 (2H, ABq, J=8.4 Hz), 7.04 (2H, ABq, J=8.5 Hz), 6.695 (1H, dd, J=17.6 and 11.0 Hz), 5.695 (1H, d, J=17.6 Hz), 5.235 (1H, d, J=10.9 Hz), 2.29 (3H, s)

Example 18

Preparation of 3,4-Diacetoxystyrene by Decarboxylation of 3,4-Dihydroxycinnamic Acid Followed by Acetylation in a Single Vessel Reaction The purpose of this Example was to prepare 3,4-diacetoxystyrene using the thermal, base-catalyzed decarboxylation of 3,4-dihydroxycinnamic acid, followed by acetylation of the resulting 3,4-hydroxystyrene with acetic anhydride in a two-step, single vessel reaction. Prostab® 5415 at a concentration of 1000 ppm was used as the polymerization inhibitor.

To a 1 L, 3-neck round-bottom flask under nitrogen and with mechanical mixing, was added 0.5 g of Prostab® 5415, 2.725 g of potassium acetate, and 50.0 g of 3,4-dihydroxycinnamic acid. DMF (280 mL) was then added, resulting in a dark brown solution. This reaction mixture was heated to 100° C. using a water condenser. The progress of the reaction was checked periodically by withdrawing a sample and analyzing it using LC-MS. After 4.5 h, it was determined that 96.6% of the theoretical yield of the 3,4-dihydroxystyrene intermediate had formed. The reaction was heated for another 45 min. Then, 132.7 mL of acetic anhydride was added to the reaction mixture over a period of 15 min. The reaction was allowed to proceed for another 15 min, after which the reaction mixture was cooled to room temperature over 45 min.

The reaction mixture was poured into a beaker containing approximately 400 mL of water and then extracted three times with diethylether. The combined organic layer from these extractions was extracted three times with 2% NaHCO$_3$ solution, followed by one extraction with brine. The organic layer was dried over Na$_2$SO$_4$, filtered and concentrated by evaporation on a rotary evaporator at 40° C. for 1 h to give 95.2 g of a dark brown oil. The oil was stored at −20° C. overnight. Then, the oil was distilled using vacuum distillation at 105-107° C. at a pressure of 1.3 mPa to give 45.11 g of a clear, viscous liquid (79.1% of the theoretical yield). The 3,4-diacetoxystyrene product was analyzed by $^1$H NMR and LC-MS and found to be 99.7% pure.

$^1$H NMR (500 MHz, CDCl$_3$): δ (ppm) 7.26 (1H, dd, J=8 and 2 Hz), 7.22 (1H, d, J=2 Hz), 7.13 (1H, d, J=9 Hz), 6.65 (1H, dd, J=18 and 11 Hz), 5.68 (1H, dd, J=18 and 1 Hz), 5.26 (1H, d, J=11 Hz), 2.27 (3H, s), 2.26 (3H, s).

Example 19

Preparation of 4-Hydroxystyrene by Decarboxylation of Para-hydroxycinnamic Acid in the Absence of a Polymerization Inhibitor The purpose of this Example was to prepare 4-hydroxystyrene by the thermal, base-catalyzed decarboxylation of concentrated para-hydroxycinnamic acid (4 m or 2.54 M) using potassium acetate (1 mol %) as the basic catalyst in DMAc in the absence of a polymerization inhibitor.

To a 3-neck, round-bottom flask was added pHCA (20.035 g, 122.05 mmol) and 30.034 g of DMAc (to make a 2.54 M solution of pHCA). The reaction flask was lowered into a preheated oil bath at 150° C. and the solution reached temperature after approximately 15 min. Potassium acetate (0.124 g, 1 mol %) was added all at once. The reaction was performed under nitrogen with stirring and with a reflux condenser for 8 h. Samples were taken just before addition of potassium acetate (time 0) and at 15 min, 30 min, 1 h, 2 h, 4 h, 6 h, and 8 h and analyzed by HPLC for pHCA and pHS using Method 2, as described above. The results, given in Table 5, show that conversion of pHCA was essentially complete after 4 h, and the yield of pHS at that time was 87.1%.

TABLE 5

HPLC Determinations of pHCA and pHS at Various Times

| Reaction Time (min) | pHCA (mmol) | pHS (mmol) |
| --- | --- | --- |
| 0 | 116.9 | 4.8 |
| 15 | 97.0 | 23.4 |
| 30 | 83.0 | 42.5 |
| 60 | 50.6 | 66.1 |
| 120 | 17.0 | 96.0 |
| 240 | 0.6 | 106.3 |
| 360 | 0 | 103.4 |
| 480 | 0 | 96.6 |

Examples 20-22

Preparation of 4-Hydroxystyrene by Decarboxylation of Para-hydroxycinnamic Acid Using Different Levels of Potassium Acetate as Basic Catalyst in DMAc The purpose of these Examples was to prepare 4-hydroxystyrene by the thermal, base-catalyzed decarboxylation of concentrated para-hydroxycinnamic acid (2.5 M) in DMAc using potassium acetate at different levels as the basic catalyst.

In these Examples the same procedure as described in Example 19 was used, except for the amount of potassium acetate added to the reaction solution. To a 3-neck, round-bottom flask was added pHCA (19.11 g, 116.4 mmol) and 30.0 g of DMAc (to make a 2.5 M solution of pHCA). The reaction flask was lowered into a preheated oil bath at 135° C. and the solution reached temperature after approximately 15 min. Potassium acetate (amounts given in Table 6) was added all at once. The reaction was performed under nitrogen with stirring and with a reflux condenser for 4 to 6 h. Samples were taken just before addition of potassium acetate (time 0) and at 15 min, 30 min, 1 h, 2 h, 4 h, and 6 h and analyzed by HPLC for pHCA and pHS using Method 2, as described above. For Comparative Example 22 without potassium acetate, time 0 was taken to be the time at which the temperature of the reaction solution had equilibrated to 135° C.

TABLE 6

HPLC Determinations of pHCA and pHS at Various Times in Reactions With Different Levels of Potassium Acetate

| | Example 20 | | Example 21 | | Comparative Example 22 | |
|---|---|---|---|---|---|---|
| | Potassium Acetate | | | | | |
| | 1.146 g (10 mol %) | | 2.860 g* (25 mol %) | | 0 (0 mol %) | |
| Reaction Time (min) | pHCA (mmol) | pHS (mmol) | pHCA (mmol) | pHS (mmol) | pHCA (mmol) | pHS (mmol) |
| 0 | 113.3 | 0 | 114.3 | 0 | 114.2 | 0 |
| 15 | 87.0 | 26.7 | 67.6 | 46.4 | 114.7 | 1.5 |
| 30 | 63.4 | 50.0 | 35.8 | 79.2 | 112.1 | 3.7 |
| 60 | 28.5 | 84.7 | 8.3 | 105.2 | 105.0 | 8.8 |
| 120 | 4.7 | 107.9 | 0.5 | 102.1 | 95.9 | 18.3 |
| 240 | 0 | 102.1 | 0 | 88.7 | 76.9 | 34.1 |
| 360 | 0 | 89.5 | 0 | 71.9 | nd | nd |

*Solids, identified as potassium acetate, precipitated between 60 and 120 min in Example 21.

As can be seen from the results given in Table 6, Example 20 gives a yield of pHS of 92.7% after 2 h, and Example 21 gives a yield of pHS of 90.4% after 1 h. Both examples show complete conversion of pHCA in less than 4 h. By contrast, Comparative Example 22, run under the same conditions except without the basic catalyst, shows a yield of pHS of only 29.3% and a conversion of pHCA of only 33.9% even after 4 h.

Example 23

Preparation of 4-Hydroxystyrene by Decarboxylation of Para-hydroxycinnamic Acid Using Potassium Acetate as Basic Catalyst in Di(Propylene Glycol) Methyl Ether The purpose of this Example was to prepare 4-hydroxystyrene by the thermal, base-catalyzed decarboxylation of para-hydroxycinnamic acid (2.5 m) using potassium acetate (10 mol %) as the basic catalyst in the protic solvent di(propylene glycol) methyl ether (Dowanol™ DPM; Dow Chemical Co., Midland, Mich.).

To a 3-neck, round-bottom flask was added pHCA (12.318 g, 75.04 mmol) and 30.052 g of di(propylene glycol) methyl ether (to make a 2.5 m solution of pHCA). The reaction flask was lowered into a preheated oil bath at 135° C. and the solution reached temperature after approximately 15 min. The pHCA fully dissolved upon heating of the solution. Potassium acetate (0.739 g, 10 mol %) was added all at once. The reaction was performed under nitrogen with stirring and with a reflux condenser for 8 h. Solids formed upon adding the base, increased until approximately 3 h, and then were again fully dissolved by approximately 5 h. Samples were taken just before addition of potassium acetate (time 0) and at 15 min, 30 min, 1 h, 2 h, 4 h, 6 h, and 8 h and analyzed by HPLC for pHCA and pHS using Method 2, as described above. The results (see Table 7) show that the yield of pHS after 2 h was 67.3%. Additional reaction time reduced the yield. This result demonstrates that a protic solvent may be used in the thermal decarboxylation reaction.

TABLE 7

HPLC Determinations of pHCA and pHS at Various Times in a Reaction Using Di(propylene glycol) Methyl Ether as Solvent

| Reaction Time (min) | pHCA (mmol) | pHS (mmol) |
|---|---|---|
| 0 | 73.5 | 0 |
| 15 | 60.6 | 12.0 |
| 30 | 46.2 | 21.9 |
| 60 | 31.6 | 38.0 |
| 120 | 12.3 | 50.5 |
| 240 | 2.2 | 45.9 |
| 360 | 0 | 17.7 |
| 480 | 0 | 7.2 |

Example 24

Preparation of 4-Hydroxystyrene by Decarboxylation of Para-hydroxycinnamic Acid Using Potassium Acetate as Basic Catalyst in DMF with Microwave Heating The purpose of this Example was to prepare 4-hydroxystyrene by the thermal, base-catalyzed decarboxylation of para-hydroxycinnamic acid using potassium acetate as the basic catalyst in DMF in the presence of a polymerization inhibitor (1000 ppm Prostab® 5415). This example utilizes microwave heating, resulting in higher temperatures and shorter reaction times.

To a 5 mL Biotage test tube vial (Biotage AB, Charlottesville, Va.) equipped with a stir bar was added pHCA (1.002 g, 6.104 mmol), 3 mL DMF (to make an approximately 2 M solution of pHCA), 1000 ppm Prostab® 5415 (1 mg), and potassium acetate (63 mg, 10 mol %). Nitrogen was blown into the test tube, and the tube was quickly crimp-capped. The sealed vial was placed into a Biotage Initiator 60 microwave reactor (Biotage AB). Under medium power of 150 watts, the sample temperature reached 190° C. after a 70-80 sec heat-up period. The sample was held at 190° C. for 3 min, with a brief period of overshooting to approximately 200° C. The sample pressure reached 16 bar (1600 kPa) during the run. Qualitative HPLC of the exposed sample using Method 3, as described above, showed complete conversion of pHCA; there was no pHCA detected over the UV spectral range of 220 to 312 nm. The peak due to pHS was 73.3 area % at 220 nm and 100 area % at 312 nm, indicating good selectivity of the reaction.

Example 25

Preparation of 4-Acetoxystyrene by Decarboxylation of Para-hydroxycinnamic Acid Followed by Acetylation in a Single Vessel Reaction The purpose of this Example was to prepare 4-acetoxystyrene using the thermal, base-catalyzed decarboxylation of para-hydroxycinnamic acid, followed by acetylation of the resulting 4-hydroxystyrene with acetic anhydride in a two-step, single vessel reaction. No inhibitor was used for this Example, and the starting pHCA was approximately 85% pure derived from the bio-conversion of tyrosine.

The starting pHCA material was produced using a method similar to that described by Ben Bassat et al. in copending and commonly owned U.S. Patent Application No. 60/563,633. That method involves a two-stage process to produce pHCA from glucose. In the method used in this Example, the two stages were done as two separate steps. In the first step, tyrosine was produced from glucose by fermentation using a tyrosine overproducing strain. The tyrosine was separated from the fermentation broth using low speed centrifugation. The resulting precipitate was suspended in water and separated again using low speed centrifugation. The purity of the tyrosine was estimated to be 90-98% using HPLC. Then, in the second stage, the tyrosine was converted to pHCA at pH 10.0 using a host cell comprising an enzyme having tyrosine ammonia lyase activity. The pHCA accumulated in the fermentation medium. About 7.5 kg of the pHCA-containing broth was centrifuged and the solids were discarded. The supernatant was transferred to a 14 L Braun fermentor, Bio-Stat C.B. (Braun Biotech International, Melesungen, Germany) operated at 35° C. and 600 rpm. The pH of the solution was adjusted to 9.0 using sulfuric acid. Then, 0.254 mL of Alcalase®) (Novozymes, Krogshoejvej 36, 2880 Bagsvaerd, Denmark) and 0.134 g of Bromelain (Acros Organics, obtained from Fisher Scientific, Pittsburgh, Pa.) were added. After a 1 h incubation, the solution was titrated to pH 2.2 to precipitate the pHCA. The resulting suspension was centrifuged and the pHCA was recovered as a 600 g wet cake with approximately 40% solids. In addition to the pHCA, the wet cake also contained proteins, cell debris, salts, approximately 0.21% cinnamic acid, and 0.1% tyrosine. The wet cake was dried at 80° C. for 12 h under nitrogen to give a dried cake, which contained approximately 85% pHCA.

The bioproduced pHCA was purified by extraction as follows. To a 1 L kettle was added 163.88 g of the dried cake containing pHCA. To the kettle was added 350 mL DMAc and the contents were heated to 60° C. for 2 h with mechanical stirring. The mixture was filtered through Whatmann No. 4 paper and the insolubles were washed with 50 mL DMAc.

The combined filtrate and washings from the extraction were added to a 1 L 4-neck flask equipped with an overhead stirrer, a reflux condenser, an addition funnel, and a temperature probe. The reaction mixture was assayed by HPLC Method 4, described above, and found to contain 122.98 g pHCA. To the mixture was added 8.8 g (10 mol %) of potassium acetate and the mixture was heated to 135° C. under nitrogen for 3 h. Acetic anhydride, 91.77 g, 84.97 mL was added via addition funnel over 8 min. The reaction mixture was stirred for an additional 0.5 h and then allowed to cool to room temperature. The solvent was removed on a rotary evaporator at 2.8 torr (0.37 kPa) and 65° C. A solid separated from the mixture and was filtered off using Whatmann No. 4 paper. The solid was washed with 30 mL DMAc. The combined filtrates were further concentrated on a rotary evaporator at 2.5 torr (0.33 kPa) and 65° C. until no more solvent distilled off.

The crude pAS thus obtained, 157.5 g, was stabilized by addition of 200 ppm methyl hydroquinone, and distilled on a thin film evaporator (model KDL-4 with 0.04 m² surface area from UIC Inc. 1225 Channahon Rd., Joliet, Ill. 60436). The distillation was performed at 2.00 mm Hg (0.267 kPa) with a feed rate of 2.0 mL/min and a stirring rate of 300 rpm. The inlet temperature was 71° C., the outlet temperature was 70° C., and the coldfinger was maintained at 10° C. The pAS was in the overheads along with residual DMAc, 112.9 g, and the heavy fraction (27.6 g) contained pAS and its oligomers, formed during the final distillation. The DMAc was removed from the overhead fraction by distillation at 0.02 torr (2.7 Pa) and 45° C. to give 86.2 g (71% yield) of pAS.

What is claimed is:

1. A method for the decarboxylation of a phenolic substrate to produce a vinyl monomer comprising the steps of:
   a) providing a phenolic substrate having the general structure:

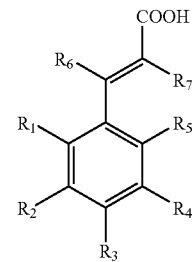

wherein $R_1$, $R_3$, and $R_5$ are H, OH, or $OCH_3$; $R_2$, and $R_4$ are H, OH, $OCH_3$ or linear or branched alkyl; $R_6$ and $R_7$ are H, halo, or cyano provided that at least one of $R_1$, $R_3$, or $R_5$ is OH, and that $R_2$, and $R_4$ are not both simultaneously t-butyl;
   b) providing a substantially anhydrous reaction mixture consisting essentially of:
      i) a non-amine basic catalyst present in catalytic amounts; and
      ii) at least one polar organic solvent or polar organic solvent mixture; and
   c) contacting the phenolic substrate of step a) with the reaction mixture of step b) at a temperature of at least about 100° C. for a time sufficient for the decarboxylation of the phenolic substrate to produce a stable vinyl monomer wherein the decarboxylation is carried out in a substantially anhydrous reaction medium; and
   d) optionally isolating the stable vinyl monomer of step c.

2. A method according to claim 1 wherein $R_3$ is OH.

3. A method according to claim 1 wherein the phenolic substrate is selected from the group consisting of 4-hydroxycinnamic acid, ferulic acid, sinapinic acid, caffeic acid, 2-hydroxycinnamic acid, and α-cyano-4-hydroxycinnamic acid.

4. A method according to claim 1 wherein the vinyl monomer is selected from the group consisting of 4-hydroxystyrene, 3-methoxy-4-hydroxystyrene, 3,5-dimethoxy-4-hydroxystyrene, 3,4-dihydroxystyrene, 2-hydroxystyrene and α-cyano-4-hydroxystyrene.

5. A method according to claim 1 wherein the non-amine basic catalyst comprises potassium.

6. A method according to claim 1 wherein the non-amine basic catalyst is an acetate salt.

7. A method according to claim 1 wherein the non-amine basic catalyst is a metallic salt.

8. A method according to claim 7 wherein the non-amine basic catalyst is selected from the group consisting of potassium acetate, potassium carbonate, potassium hydroxide, sodium acetate, sodium carbonate, sodium hydroxide and magnesium oxide.

9. A method according to claim 1 wherein the non-amine basic catalyst is at a concentration of about 1 mol % to about 30 mol % relative to the substrate in the reaction mixture.

10. A method according to claim 1 wherein the polar organic solvent is aprotic.

11. A method according to claim 10 wherein the aprotic, polar organic solvent is selected from the group consisting of N,N-dimethylformamide, 1-methyl-2-pyrrolidinone, N,N-dimethylacetamide, dimethylsulfoxide, hexamethylphosphoramide, and hexamethylphosphorous triamide.

12. A method according to claim 1 wherein the polar organic solvent is protic.

13. A method according to claim 12 wherein the protic solvent is selected from the group consisting of di(propylene glycol) methyl ether, di(ethylene glycol) methyl ether, 2-butoxyethanol, ethylene glycol, 2-methoxyethanol, propylene glycol methyl ether, n-hexanol, and n-butanol.

14. A method according to claim 1 wherein the reaction mixture optionally comprises a polymerization inhibitor.

15. A method according to claim 14 wherein the polymerization inhibitor is selected from the group consisting of hydroquinone, hydroquinone monomethylether, 4-tert-butyl catechol, phenothiazine, N-oxyl (nitroxide) inhibitors, 4-hydroxy-TEMPO (4-hydroxy-2,2,6,6-tetramethylpiperidin-1-yloxy and 1,6-hexamethylene-bis(N-formyl-N-(1-oxyl-2,2,6,6-tetramethylpiperidine-4-yl)amine.

16. A method according to claim 15 wherein the polymerization inhibitor is (bis(1-oxyl-2,2,6,6-tetramethylpiperidine-4-yl)sebacate.

17. A method according to claim 1 wherein the reaction mixture optionally comprises a polymerization retarder.

18. A method according to claim 17 wherein the polymerization retarder is selected from the group consisting of dinitro-ortho-cresol (DNOC) and dinitrobutylphenol (DNBP).

19. A method according to claim 1 wherein the yield of the vinyl monomer is greater than 63%.

20. A method according to claim 1 wherein the temperature is about 100° C. to about 200° C.

* * * * *